(12) United States Patent
Kim et al.

(10) Patent No.: US 9,737,284 B2
(45) Date of Patent: Aug. 22, 2017

(54) PHANTOM FOR MEASURING THICKNESS OF THIN LAYER USING ULTRASONIC IMAGING DEVICE AND METHOD OF USING THEREOF

(71) Applicant: Korea Research Institute of Standards and Science, Daejeon (KR)

(72) Inventors: Yong Tae Kim, Daejeon (KR); Bong Young Ahn, Daejeon (KR); Il Doh, Daejeon (KR); Wuon-Shick Kim, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 482 days.

(21) Appl. No.: 14/522,351

(22) Filed: Oct. 23, 2014

(65) Prior Publication Data

US 2016/0113634 A1  Apr. 28, 2016

(51) Int. Cl.
*A61B 8/00* (2006.01)
*G01N 29/30* (2006.01)

(52) U.S. Cl.
CPC ............. *A61B 8/587* (2013.01); *G01N 29/30* (2013.01); *G01N 2291/02475* (2013.01)

(58) Field of Classification Search
CPC ..................................................... A61B 8/587
See application file for complete search history.

(56) References Cited

U.S. PATENT DOCUMENTS

| | | | | |
|---|---|---|---|---|
| 5,756,875 A | * | 5/1998 | Parker | A61B 8/587 367/13 |
| 6,238,343 B1 | * | 5/2001 | Madsen | A61B 8/00 600/437 |
| 2002/0012999 A1 | * | 1/2002 | Madsen | A61B 8/08 436/8 |
| 2008/0076099 A1 | * | 3/2008 | Sarvazyan | G09B 23/30 434/262 |
| 2008/0214936 A1 | * | 9/2008 | Wieringa | A61B 5/0059 600/443 |
| 2013/0139567 A1 | * | 6/2013 | Madsen | G01N 29/265 73/1.86 |

* cited by examiner

*Primary Examiner* — Manuel L Barbee
*Assistant Examiner* — Raymond Nimox
(74) *Attorney, Agent, or Firm* — Kaplan Breyer Schwarz, LLP

(57) ABSTRACT

A phantom for measuring thickness of a thin layer and a method of using thereof. The phantom may include a non-scattering muscle mimicking material having a flat top surface; a plurality of soft tissue mimicking thin layers placed in a first area, which is at least a part of a top surface of the non-scattering muscle mimicking material, and having thicknesses different from each other; and an anechoic blood mimicking liquid material placed in an area other than the first area among an entire area of the top surface of the non-scattering muscle mimicking material and on a top surface of the plurality of soft tissue mimicking thin layers.

7 Claims, 14 Drawing Sheets

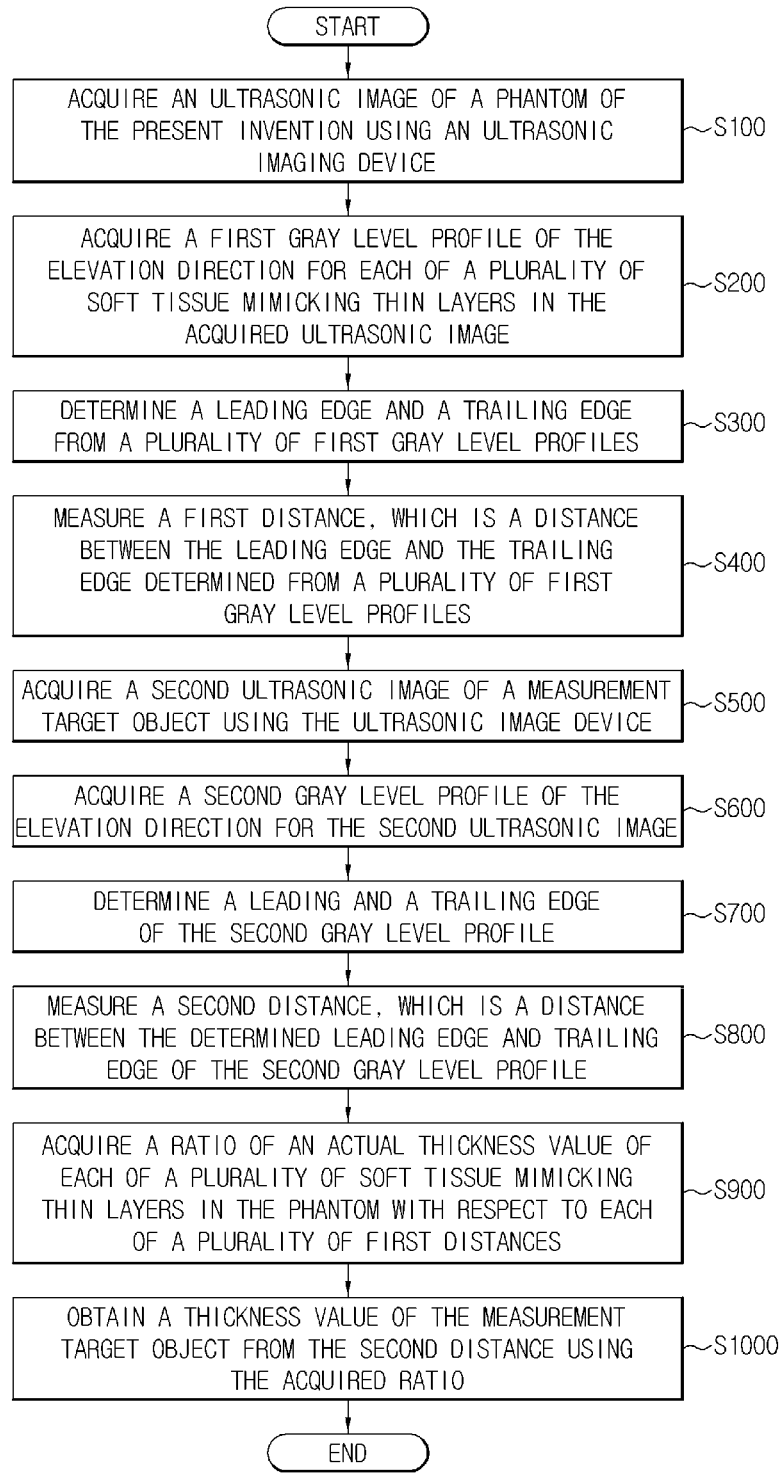

PHANTOM FOR MEASURING THICKNESS OF THIN LAYER USING ULTRASONIC IMAGING DEVICE AND METHOD OF USING THEREOF

FIELD OF THE INVENTION

The present invention relates to a phantom for measuring thickness of a thin layer and a method of using thereof, and more specifically, to "a phantom including a plurality of thin layers having different thickness" to measure thickness of a thin layer 0.5 to 3 times as thick as an ultrasonic wavelength and "a method of measuring thickness of a thin layer using an ultrasonic imaging device and a phantom including a plurality of thin layers having thicknesses different from each other".

BACKGROUND OF THE INVENTION

An ultrasonic wave is a sound wave which cannot be heard since its frequency is beyond a threshold frequency that a human being can hear as a sound, and since the ultrasonic wave has a short wavelength and high directionality, it can be used in a sonar for measuring depth of a sea, a fish detector or the like by generating a pulse thereof. In addition, in the same principle, the ultrasonic wave can be used to inspect internal defects of a solid material, to cut or process gem/glass or the like, or to create, cleanse and sanitize emulsion.

In addition to this, abnormalities in a human tissue or an animal tissue can be detected using the ultrasonic wave, and there are ultrasonic imaging devices for diagnosing the abnormalities. This makes it possible to confirm the abnormalities in the body of a living creature without dissecting the body. For example, degrees of fatness of organ tissues or thickness of abdominal fat layers can be confirmed by acquiring ultrasonic images of organs of a human body.

Since such an ultrasonography is relatively cheap and convenient to take images and, fundamentally, it does not use radiation, it is safe and non-invasive. Nevertheless, it is disadvantageous in that photographing conditions and photographing techniques are absolutely influential to the quality of ultrasonic images, and reflection characteristics and resolution of the parts through which the ultrasonic waves pass are irregular. Therefore, when various kinds of diagnoses are performed using the photographed images, it is highly probable that a diagnostician arbitrarily interpretes the images, and thus reliability of diagnoses is not perfectly guaranteed.

A phantom used for calibrating an ultrasonic imaging device has been proposed to solve such a problem.

FIG. 1 is a view showing a conventional thickness phantom, and the phantom of FIG. 1 contains a thin plane of a single thickness configured of an echo genic material at a slope of 45 degrees within an anechoic tissue mimicking material.

In order to calibrate an ultrasonic imaging device, the thin plane is scanned using a probe of the ultrasonic imaging device in the direction of 45-degree scan plane from the top surface of the conventional phantom, and a distance to the echo genic line of the acquired image is used as a depth. Since the thin plane is embedded at an angle of 45 degrees, depth to the thin plane from the top surface of the phantom varies depending on the horizontal position of the probe. Accordingly, the ultrasonic imaging device is calibrated by acquiring images while varying the horizontal position of the probe and using a ratio of an actual distance to the thin plane from the top surface of the phantom with respect to the distance to the echo genic line within the image.

If such a conventional phantom is used, an ultrasonic image device which measures a depth several tens of times as thick as a wavelength can be calibrated, and thus a size of an organ in a human body, a size of a fetus in the body of a pregnant woman or the like can be measured approximately.

However, there is a problem in that if the conventional phantom and a method of measuring thickness are used to measure a thickness 0.5 to 3 times as thick as an ultrasonic wavelength, an error occurs in a measured value.

Particularly, thickness of intima, media and intima-media of a blood vessel is used as a diagnostic symptom of a cardiovascular disease and an endocrine system disease, and since thickness of the intima, media and intima-media of a blood vessel cannot be measured using the conventional phantom and the method of measuring thickness, it may create further problems.

Accordingly, required is development of a phantom which can be used to measure thickness of a thin layer 0.5 to 3 times as thick as an ultrasonic wavelength.

SUMMARY OF THE INVENTION

Therefore, the present invention has been made in view of the above problems, and it is an object of the present invention to provide a user with a phantom and a method of measuring thickness, which can measure thickness of a very thin target object.

Specifically, an object of the present invention is to provide a user with a phantom and a method of measuring thickness, which can measure a thickness 0.5 to 3 times as thick as an ultrasonic wavelength using an ultrasonic imaging device.

In addition, another object of the present invention is to provide a user with a method of obtaining a leading edge and a trailing edge by using Hilbert transform.

In addition, still another object of the present invention is to provide a user with a phantom and a method of measuring thickness, which can measure thickness of a target object even when width of an ultrasonic wave pulse varies depending on ultrasonic imaging devices.

However, technical problems to be accomplished in the present invention are not limited to the technical problems mentioned above, and unmentioned other technical problems will be clearly understood by those skilled in the art from the following descriptions.

To accomplish the above objects, according to one aspect of the present invention, there is provided a phantom used for calibrating an ultrasonic image of an ultrasonic imaging device, the phantom including: a non-scattering muscle mimicking material having a flat top surface; a plurality of soft tissue mimicking thin layers placed in a first area, which is at least a part of a top surface of the non-scattering muscle mimicking material, and having thicknesses different from each other; and an anechoic blood mimicking liquid material placed in an area other than the first area among an entire area of the top surface of the non-scattering muscle mimicking material and on a top surface of the plurality of soft tissue mimicking thin layers, wherein gray level profiles of ultrasonic images of the top surface and a bottom surface of the plurality of soft tissue mimicking thin layers are used to calibrate the ultrasonic images.

In addition, there may be four soft tissue mimicking thin layers, and thickness of each of the soft tissue mimicking thin layers may be ¼, ½, ¾ or 1 time as thick as an ultrasonic wavelength generated by the ultrasonic imaging device.

Meanwhile, according to another aspect of the present invention for accomplishing the above objects, there is provided a method of measuring thickness using an ultrasonic imaging device, the method including: a first step of obtaining a first ultrasonic image of the phantom; a second step of obtaining a first gray level profile of an elevation direction for each of a plurality of soft tissue mimicking thin layers in the first ultrasonic image; a third step of determining a 1-1 gray level profile for a top surface of each of the plurality of soft tissue mimicking thin layers and a 1-2 gray level profile for a bottom surface of each of the plurality of soft tissue mimicking thin layers among the plurality of first gray level profiles, and determining a leading edge which is one point of each of the plurality of 1-1 gray level profiles and a trailing edge which is one point of each of the plurality of 1-2 gray level profiles; a fourth step of measuring a first distance which is a distance between the leading edge and the trailing edge of each of the plurality of first gray level profiles; a fifth step of obtaining a second ultrasonic image of a measurement target object using the ultrasonic imaging device; a sixth step of obtaining a second gray level profile of an elevation direction for the second ultrasonic image; a seventh step of determining a 2-1 gray level profile for a top surface of the measurement target object and a 2-2 gray level profile for a bottom surface of the measurement target object among the second gray level profile, and determining a leading edge which is one point of the 2-1 gray level profile and a trailing edge which is one point of the 2-2 gray level profile; an eighth step of measuring a second distance which is a distance between the leading edge and the trailing edge of the determined second gray level profile; a ninth step of acquiring a ratio of an actual thickness value of each of the plurality of soft tissue mimicking thin layers in the phantom for the ultrasonic imaging device with respect to each of the plurality of first distances; and a tenth step of obtaining an actual thickness value of the measurement target object from the second distance using the acquired ratio.

In addition, the third step may include performing Hilbert transform on the plurality of first gray level profiles and determining the leading edge and the trailing edge of each of the plurality of first gray level profiles from a Hilbert transform value of each of the plurality of first gray level profiles, and the seventh step may include performing Hilbert transform on the second gray level profile and determining the leading edge and the trailing edge of the second gray level profile from a Hilbert transform value of the second gray level profile.

In addition, the third step may include determining two points corresponding to −20 dB of a maximum value among the Hilbert transform values of each of the plurality of first gray level profiles as the leading edge and the trailing edge of each of the plurality of first gray level profiles, and the seventh step may include determining two points corresponding to −20 dB of a maximum value of the Hilbert transform of the second gray level profile as the leading edge and the trailing edge of the second gray level profile.

In addition, the ninth step may further include a step of obtaining a curve showing actual thickness values of the plurality of soft tissue mimicking thin layers in the phantom for the ultrasonic imagimg device with respect to the plurality of first distances, and the tenth step may include obtaining a thickness value of the measurement target object from the second distance using the curve.

Meanwhile, according to still another aspect of the present invention for accomplishing the above objects, there is provided a recording medium which can be read by a digital processing device, in which a program of instructions that can be executed by the digital processing device is typically implemented to perform a method of measuring thickness using an ultrasonic imaging device, the method including: a first step of obtaining a first ultrasonic image of the phantom; a second step of obtaining a first gray level profile of an elevation direction for each of a plurality of soft tissue mimicking thin layers in the first ultrasonic image; a third step of determining a 1-1 gray level profile for a top surface of each of the plurality of soft tissue mimicking thin layers and a 1-2 gray level profile for a bottom surface of each of the plurality of soft tissue mimicking thin layers among the plurality of first gray level profiles, and determining a leading edge which is one point of each of the plurality of 1-1 gray level profiles and a trailing edge which is one point of each of the plurality of 1-2 gray level profiles; a fourth step of measuring a first distance which is a distance between the leading edge and the trailing edge of each of the plurality of first gray level profiles; a fifth step of obtaining a second ultrasonic image of a measurement target object using the ultrasonic imaging device; a sixth step of obtaining a second gray level profile of an elevation direction for the second ultrasonic image; a seventh step of determining a 2-1 gray level profile for a top surface of the measurement target object and a 2-2 gray level profile for a bottom surface of the measurement target object among the second gray level profile, and determining a leading edge which is one point of the 2-1 gray level profile and a trailing edge which is one point of the 2-2 gray level profile; an eighth step of measuring a second distance which is a distance between the leading edge and the trailing edge of the determined second gray level profile; a ninth step of acquiring a ratio of an actual thickness value of each of the plurality of soft tissue mimicking thin layers in the phantom for the ultrasonic imaging device with respect to each of the plurality of first distances; and a tenth step of obtaining an actual thickness value of the measurement target object from the second distance using the acquired ratio.

BRIEF DESCRIPTION OF THE DRAWINGS

Since the figures attached in this specification show a preferred embodiment of the present invention as an example for further understanding of the technical spirits of the present invention together with detailed descriptions of the present invention, the present invention should not be construed as limited to only the figures.

FIG. 4 is a flowchart illustrating a method of measuring thickness of a target object according to an embodiment of the present invention.

DESCRIPTION OF SYMBOLS

100: Non-scattering Muscle mimicking material
200: Anechoic blood mimicking liquid material
300: Soft tissue mimicking thin layer

DETAILED DESCRIPTION

Since measuring thickness of intima, media and intima-media of a blood vessel using an ultrasonic imaging device is useful in determining a symptom of a disease owing to the correlation of a cardiovascular disease and an endocrine system disease with thickness of the blood vessel, utilization of the ultrasonic imaging device increases.

However, although a thickness several tens of times as thick as an ultrasonic wavelength can be measured by using a conventional phantom and a conventional measurement method which are used when thickness is measured using an ultrasonic imaging device, there are a lot of shortcomings in measuring a very thin thickness about 0.5 to 3 times as thick as an ultrasonic wavelength.

Since the intima, media and intima-media of a blood vessel are very thin 0.5 to 3 times as thick as an ultrasonic wavelength, a phantom for measuring the thickness using an ultrasonic imaging device and a measurement method using the phantom will be proposed.

Hereinafter, a preferred embodiment of the present invention will be described above with reference to the drawings. In addition, the embodiment described below does not unduly limit the contents of the present invention described in the claims, and the entire configuration described in this embodiment is not necessarily considered as a means for solving the problems of the present invention.

Figure 1:
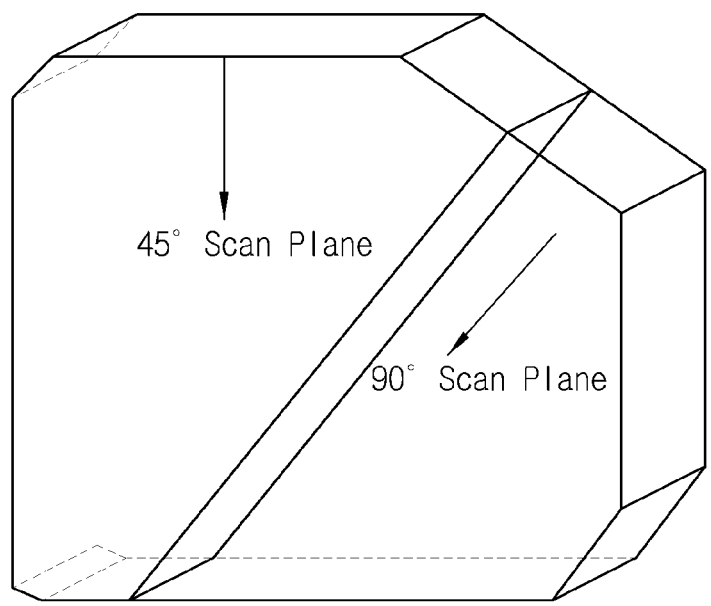
FIG. 1 is a view showing a conventional thickness phantom, and the phantom of FIG. 1 contains a thin plane of a single thickness configured of an echo genic material at a slope of 45 degrees within an anechoic tissue mimicking material.
Figure 2:
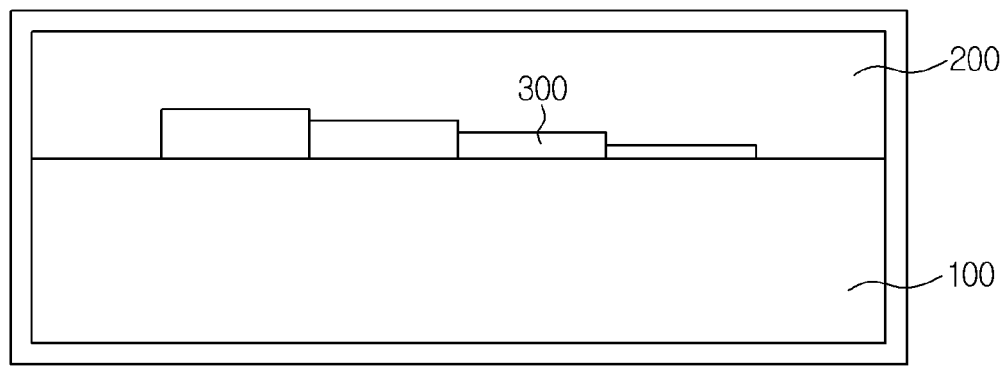
FIG. 2 is a cross sectional view showing a phantom according to an embodiment of the present invention.

FIG. 2 is a cross sectional view showing a phantom according to an embodiment of the present invention.

However, the constitutional elements shown in FIG. 2 are not indispensable, and a phantom having constitutional elements more than or less than the constitutional elements may be implemented.

A phantom is a model used in place of a human body to calibrate ultrasonic images of an ultrasonic image device, and referring to FIG. 2, it may include a non-scattering muscle mimicking material 100, an anechoic blood mimicking liquid material 200 and a plurality of soft tissue mimicking thin layers 300.

First, the non-scattering muscle mimicking material 100 is configured of a material mimicking muscles of a human body without scattering ultrasonic waves. In addition, it is configured in a predetermined thickness and may be positioned at a lowest position of the phantom as shown in FIG. 2.

Next, the anechoic blood mimicking liquid material 200 is configured of a material mimicking blood of a human body without reflecting ultrasonic waves. In addition, it can be positioned on the top of the non-scattering muscle mimicking material 100 as shown in FIG. 2.

Next, the plurality of soft tissue mimicking thin layers 300 is configured of an echo genic material, and each of the soft tissue mimicking thin layers 300 may have a different thickness. Each of the soft tissue mimicking thin layers 300 is preferably horizontally embedded between the non-scattering muscle mimicking material and the anechoic blood mimicking liquid material.

Figure 3:
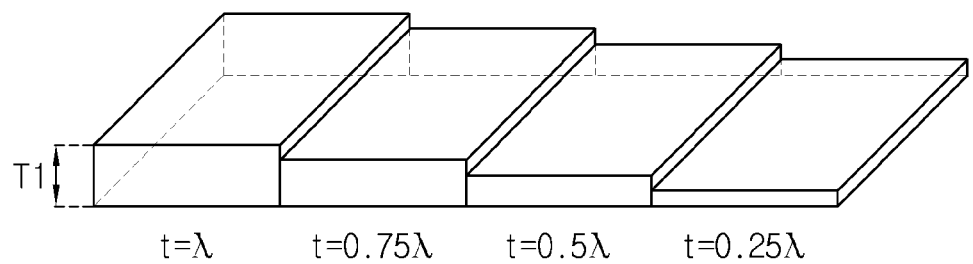
FIG. 3 is a perspective view showing a plurality of soft tissue mimicking thin layers according to an embodiment of the present invention.
Figure 5A:
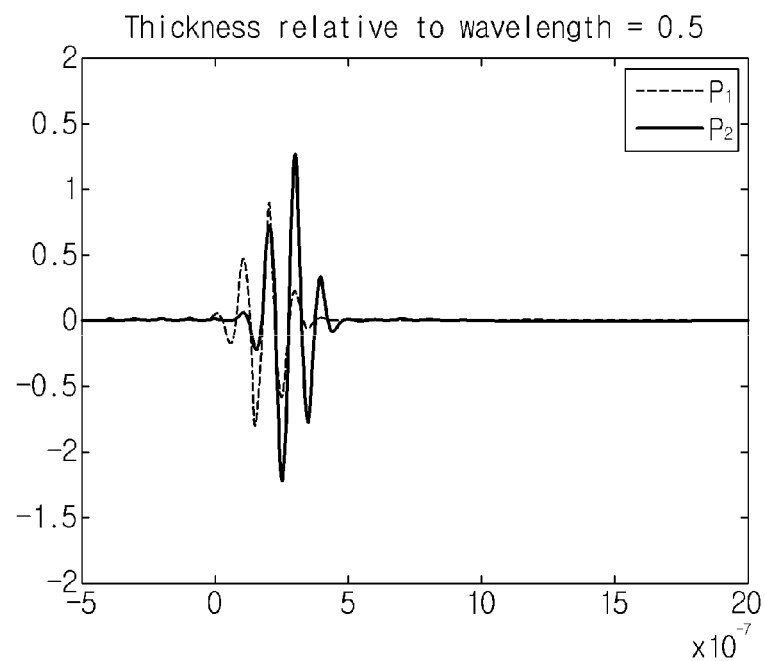
FIGS. 5a to 5h are views showing gray level profiles according to a ratio of a thickness value of a soft tissue thin layer with respect to an ultrasonic wavelength according to an embodiment of the present invention.
Figure 5B:
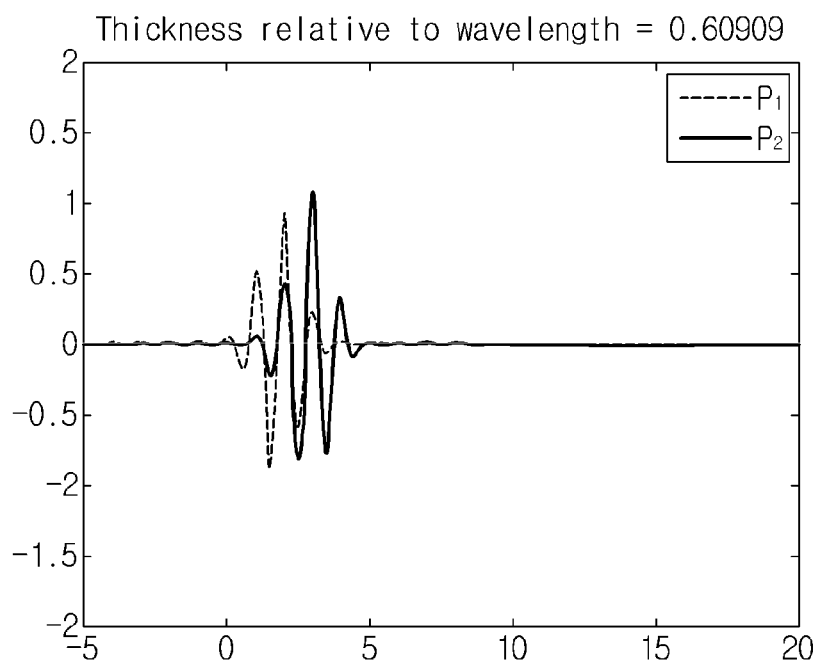
Figure 5C:
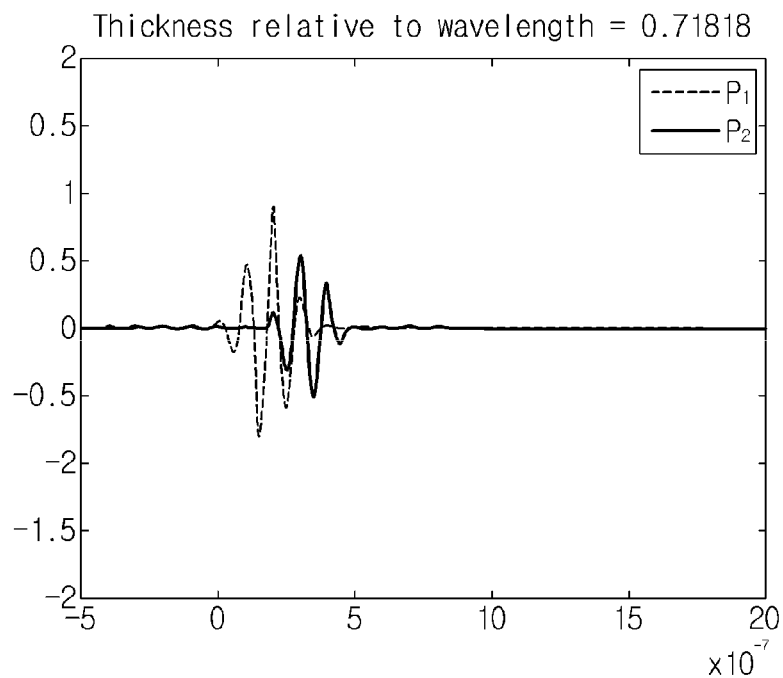
Figure 5D:
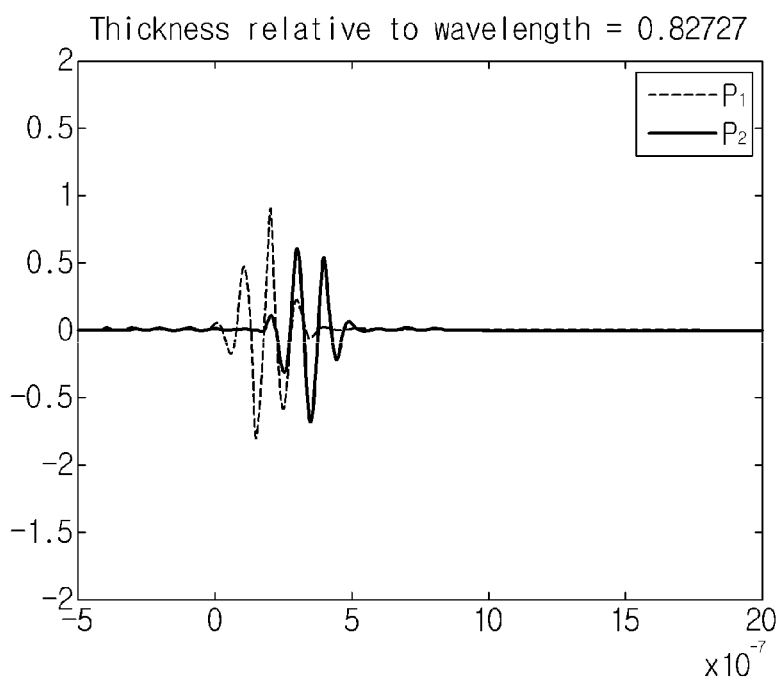
Figure 5E:
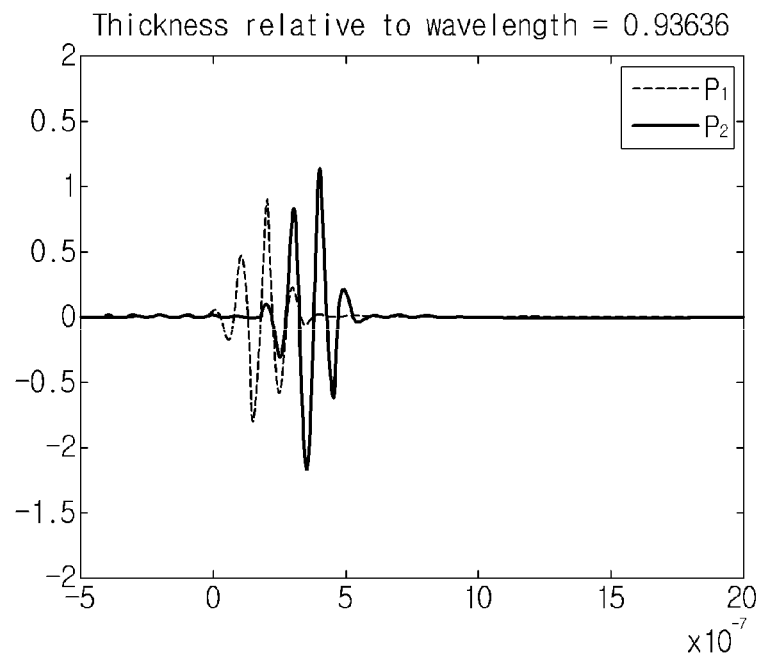
Figure 5F:
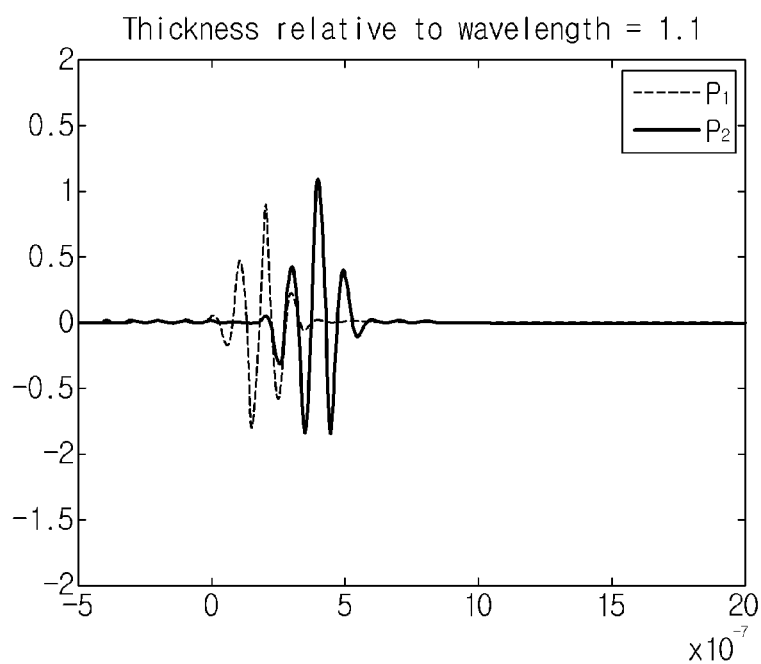
Figure 5G:
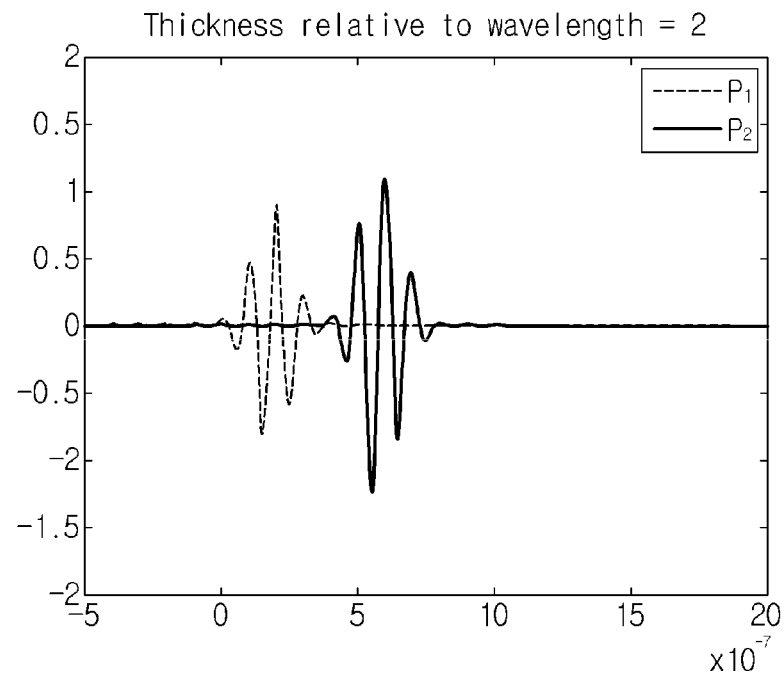
Figure 5H:
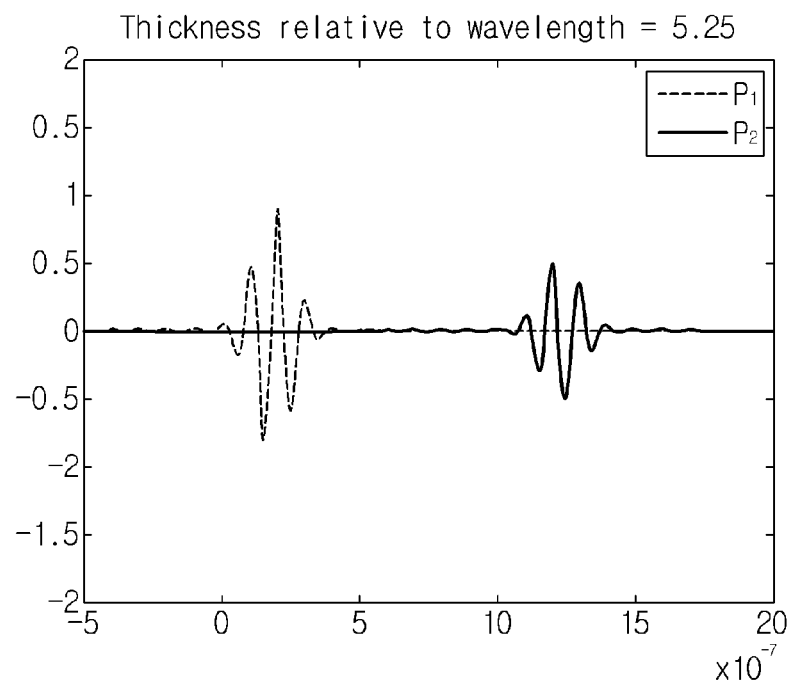
Figure 6A:
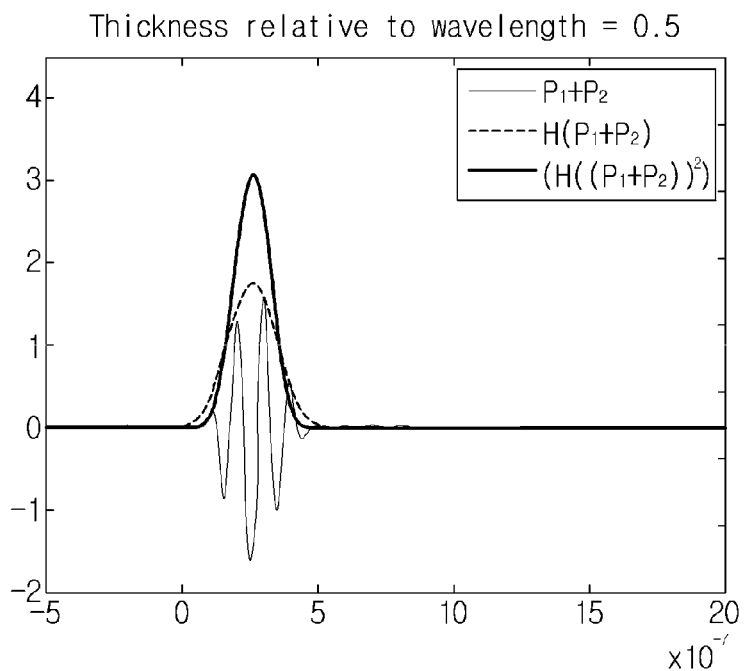
FIGS. 6a to 6h are views showing Hilbert transform of gray level profiles according to a ratio of a thickness value of a soft tissue thin layer with respect to an ultrasonic wavelength according to an embodiment of the present invention.
Figure 6B:
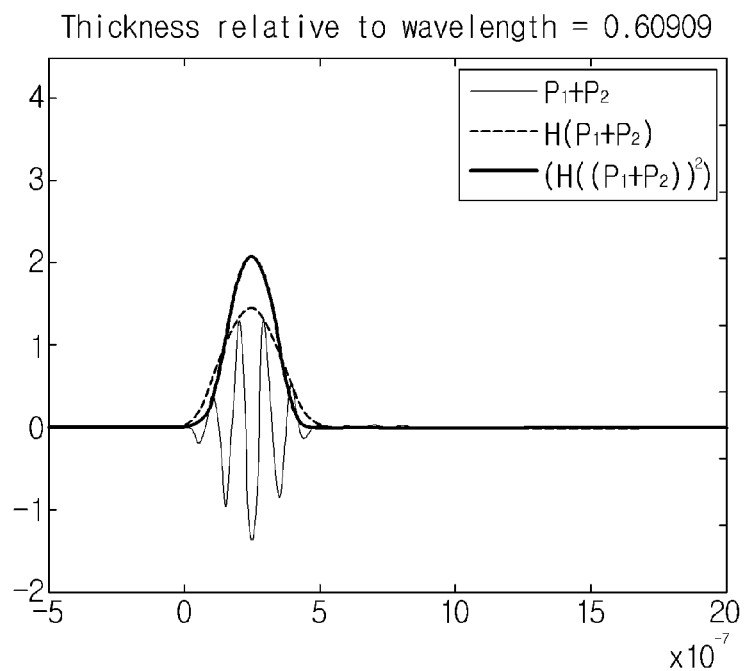
Figure 6C:
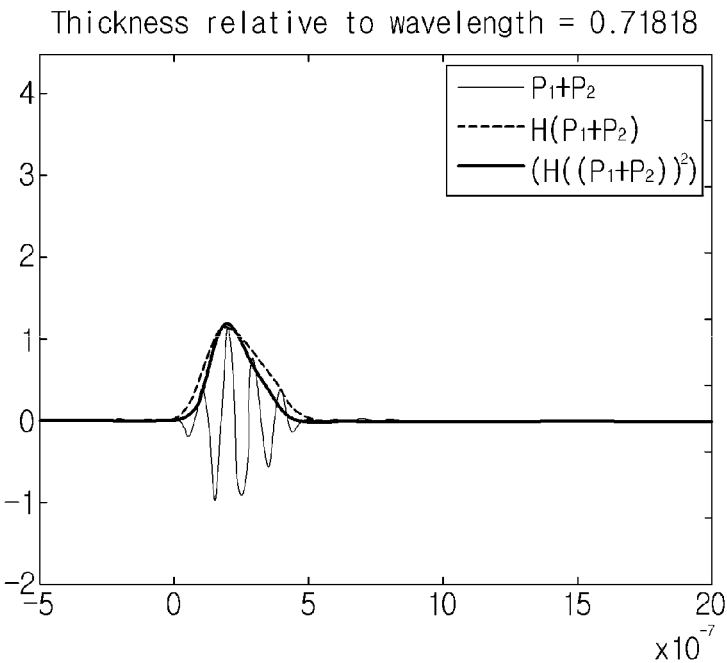
Figure 6D:
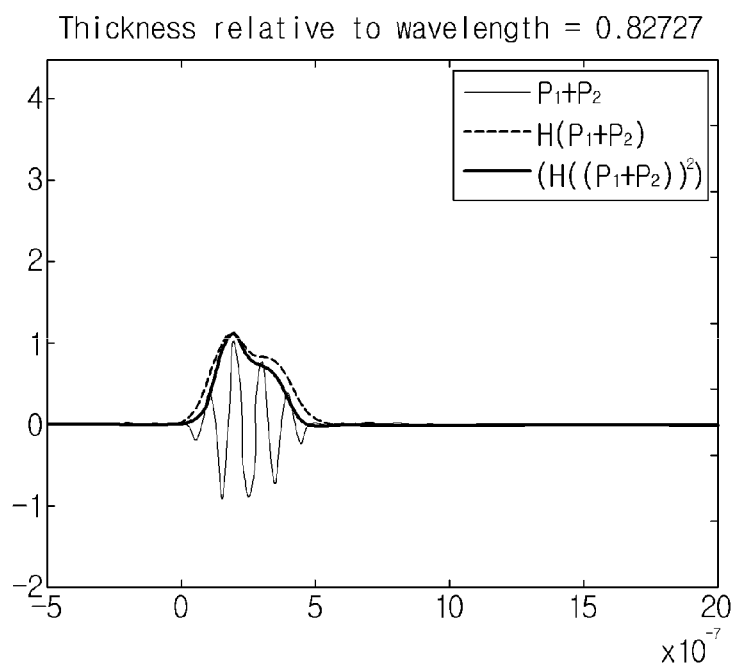
Figure 6E:
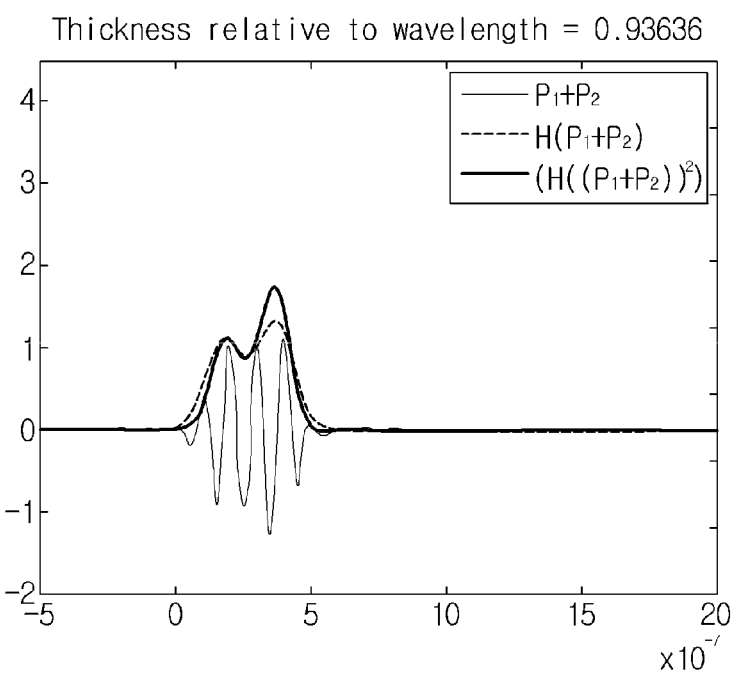
Figure 6F:
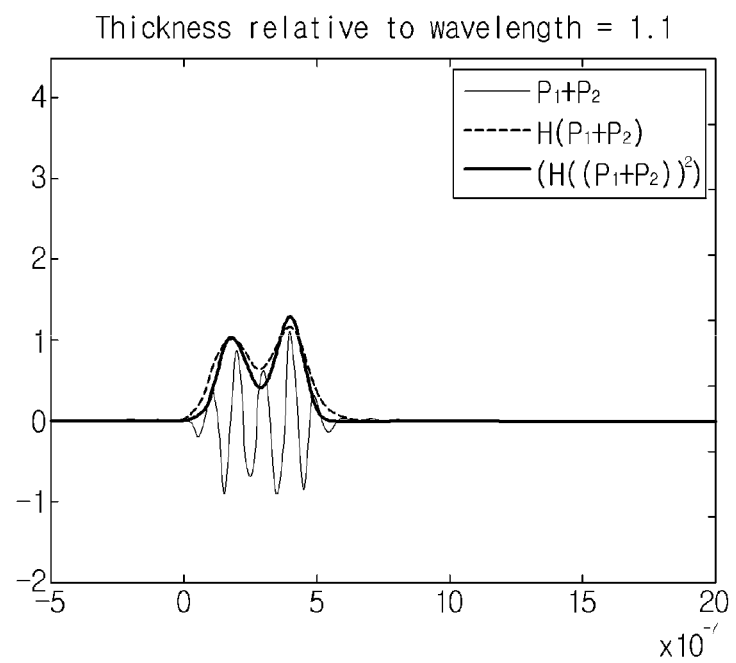
Figure 6G:
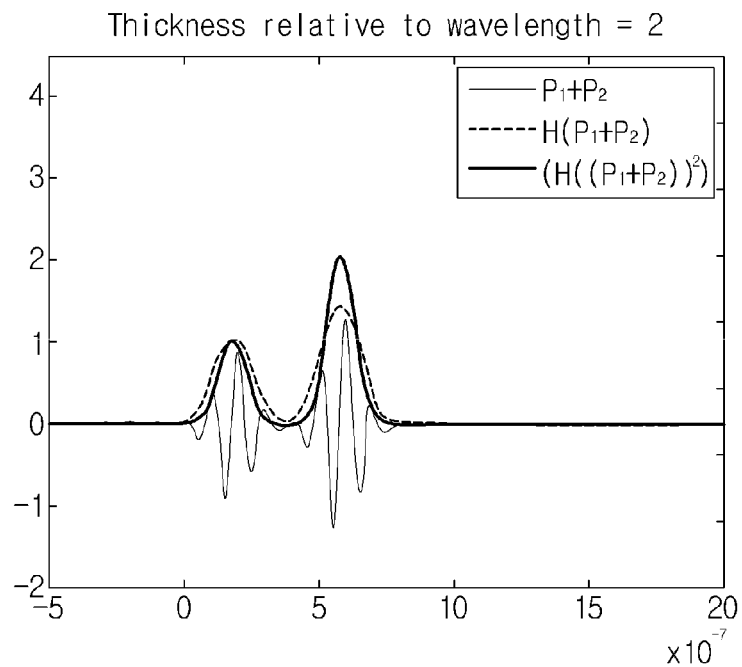
Figure 6H:
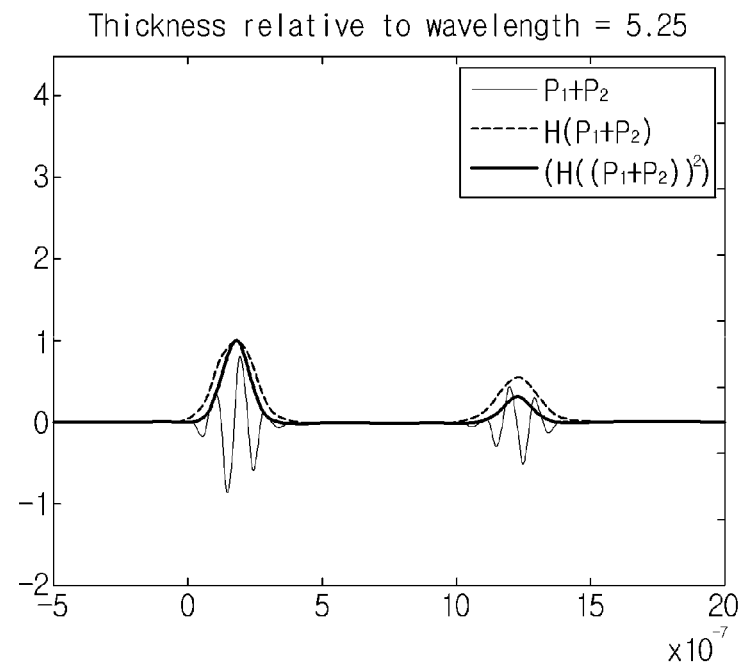
Figure 7A:
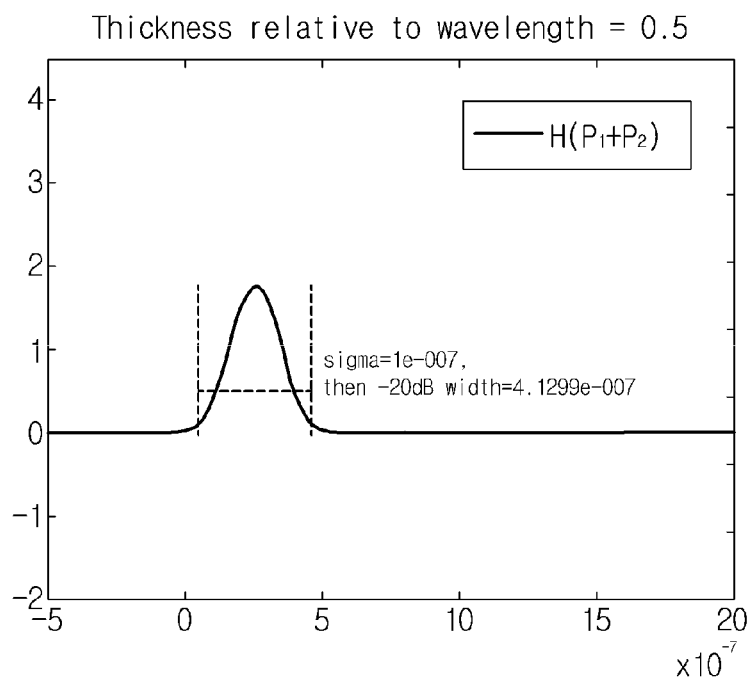
FIGS. 7a to 7d are views showing determination of a leading edge and a trailing edge from Hilbert transform according to various embodiments of the present invention.
Figure 7B:
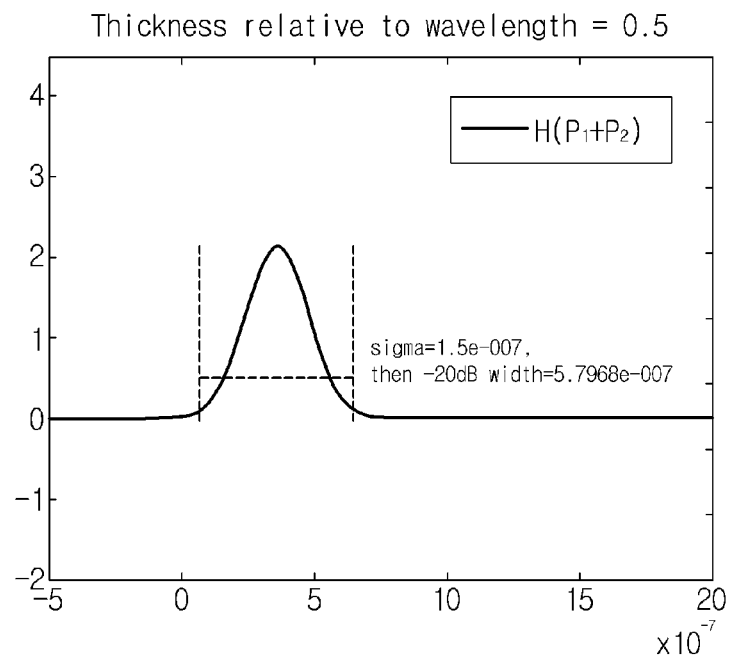
Figure 7C:
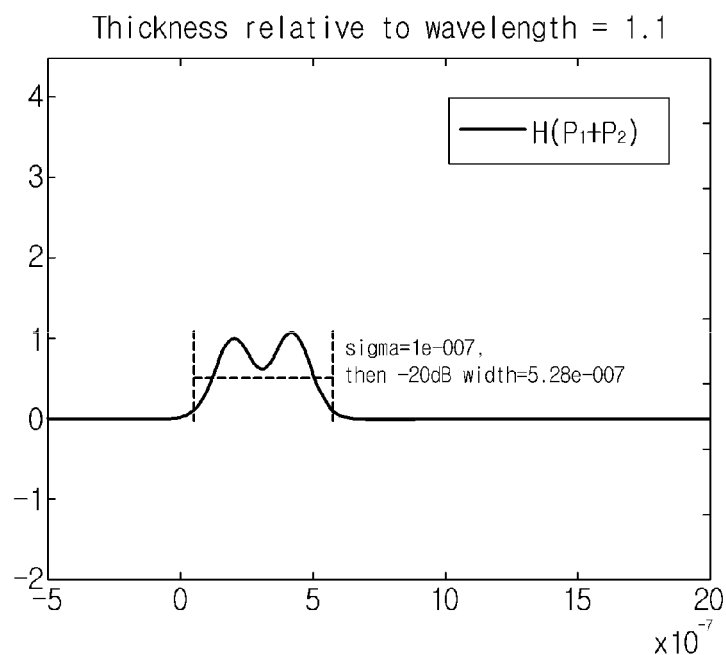
Figure 7D:
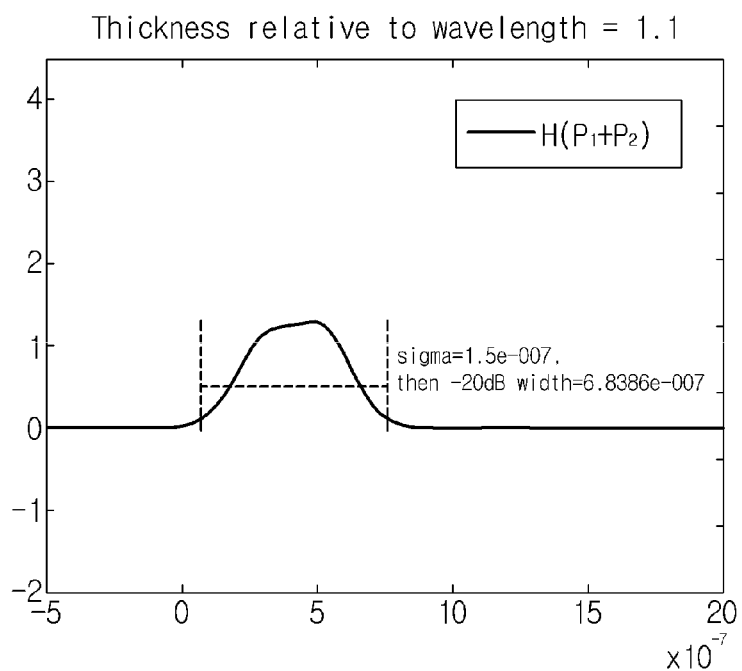

FIG. 3 is a perspective view showing a plurality of soft tissue mimicking thin layers according to an embodiment of the present invention, and referring to FIG. 3, the plurality of soft tissue mimicking thin layers 300 is configured into four, and thickness of each soft tissue mimicking thin layer 300 may be 1, ¾, ²⁄₄ or ¼ times of an ultrasonic wavelength. However, it is not limited to such an example, and in order to measure thickness of a thin layer, thickness of the soft tissue mimicking thin layer 300 is preferably formed to be less than three times of the ultrasonic wavelength.

Meanwhile, a probe which is a part of an ultrasonic image device for generating ultrasonic waves and sensing ultrasonic waves reflected from a target object, i.e., width of an ultrasonic pulse radiated from a transducer, varies according to manufacturing companies, and, furthermore, even the probes manufactured by the same manufacturing company may be different in the pulse width according to a manufacturing date and time.

Due to such a difference, although ultrasonic images are obtained for the same target object, the size of the target object may be shown differently depending on the probes.

Accordingly, a method of measuring thickness of a target object using a phantom of the present invention is needed.

Hereinafter, a method of measuring thickness using a phantom of the present invention will be described with reference to FIG. 4.

FIG. 4 is a flowchart illustrating a method of measuring thickness of a target object according to an embodiment of the present invention.

First, an ultrasonic image of a phantom of the present invention is acquired using an ultrasonic imaging device S100.

Next, a first gray level profile of the elevation direction is acquired from each of a plurality of soft tissue mimicking thin layers 300 in the acquired ultrasonic image S200.

A leading edge and a trailing edge are determined from a plurality of first gray level profiles S300.

The leading edge is one point among the gray level profiles for the top surface of the soft tissue mimicking thin layer 300, and the trailing edge one point among the gray level profiles for the bottom surface of the soft tissue mimicking thin layer 300.

That is, the leading edge and the trailing edge represent a starting point and an ending point of the thickness of the soft tissue mimicking thin layer 300.

When the leading edge and the trailing edge are determined, a 1-1 gray level profile for the top surface of the soft tissue thin layer element material and a 1-2 gray level profile for the bottom surface of the soft tissue thin layer element material are determined first from the first gray level profiles, and then the leading edge may be determined from the 1-1 gray level profile, and the trailing edge may be determined from the 1-2 gray level profile.

Hereinafter, a method of determining a leading edge and a trailing edge will be described with reference to FIGS. 5a to 5h.

FIGS. 5a to 5h are views showing gray level profiles according to a ratio of a thickness value of a soft tissue thin layer with respect to an ultrasonic wavelength according to an embodiment of the present invention.

P1 is a gray level profile of the top surface of the soft tissue mimicking thin layer 300 in an ultrasonic image, and P2 is a gray level profile of the bottom surface of the soft tissue mimicking thin layer 300 in the ultrasonic image.

Referring to FIGS. 5a to 5h, when a ratio of a thickness value of a soft tissue thin layer with respect to an ultrasonic wavelength is larger than 2, P1 and P2 are not overlapped with each other. It is since that if a soft tissue thin layer is thick, the top surface and the bottom surface of the thin layer are clearly separated in an ultrasonic image. Accordingly, when P1 and P2 are not overlapped, it may be possible to determine a maximum value point of P1 as the leading edge and a maximum value point of P2 as the trailing edge.

However, when the ratio of a thickness value of a soft tissue thin layer with respect to an ultrasonic wavelength is smaller than 2, the top surface and the bottom surface of the thin layer are not clearly separated in an ultrasonic image, and P1 and P2, which are gray level profiles, are overlapped, and thus it is difficult to determine a maximum value point for each of them.

Accordingly, when P1 and P2 are overlapped, the maximum value points thereof are not determined as a leading edge and a trailing edge, but the leading edge and the trailing edge may be determined using another method. There is a method of determining a leading edge and a trailing edge by performing Hilbert transform on the gray level profiles of the soft tissue mimicking thin layer 300. That is, the Hilbert transform is performed on the gray level profiles where P1 and P2 are overlapped.

FIGS. 6a to 6h are views showing Hilbert transform of gray level profiles according to a ratio of a thickness value of a soft tissue thin layer with respect to an ultrasonic wavelength according to an embodiment of the present invention.

Referring to FIGS. 6a to 6h, a Hilbert transform curve and a Hilbert transform square curve of the gray level profiles of the soft tissue mimicking thin layer 300 can be confirmed.

Since a gray level is proportional to the Hilbert transform of a sound intensity and the sound intensity is proportional to a square of a sound pressure, a square of the Hilbert transform should be used when a gray level profile is analyzed. However, as is confirmed in FIGS. 6a to 6h, since all Hilbert transform values have positive numbers, the Hilbert transform curve and the Hilbert transform square curve are different only in size and similar to each other in shape, and thus a Hilbert transform value can be used when a leading edge and a trailing edge are determined.

Meanwhile, when a leading edge and a trailing edge are determined using such a Hilbert transform value, it may be possible to determine two points corresponding to −20 dB of the maximum value of the Hilbert transform as the leading edge and the trailing edge.

FIGS. 7a to 7d are views showing determination of a leading edge and a trailing edge from Hilbert transform according to various embodiments of the present invention.

Referring to FIGS. 7a to 7d, two points in the graph showing Hilbert transform are points corresponding to −20 dB of the maximum value of the Hilbert transform, and the left side point is the leading edge, and the right side point is the trailing edge.

In this method, the leading edge and the trailing edge can be determined according to thickness of the soft tissue mimicking thin layer 300.

Next, a first distance, which is a distance between the leading edge and the trailing edge determined from a plurality of first gray level profiles, is measured S400.

Next, a second ultrasonic image of a measurement target object is acquired using an ultrasonic image device S500.

Next, a second gray level profile of the elevation direction is acquired from the second ultrasonic image S600.

Next, a leading and a trailing edge of the second gray level profile are determined S700.

At step S700, the leading edge is one point of the top surface gray level profile of the measurement target object, and the trailing edge is one point of the bottom surface gray level profile of the measurement target object.

The leading edge and the trailing edge may be determined by performing Hilbert transform and selecting two points corresponding to −20 dB of the maximum value of the Hilbert transform, as shown in step S300 described above.

Next, a second distance, which is a distance between the determined leading edge and trailing edge of the second gray level profile, is measured S800.

Next, a ratio of an actual thickness value of each of a plurality of soft tissue mimicking thin layers in the phantom with respect to each of a plurality of first distances is acquired S900.

That is, a ratio of an actual thickness value of each of a plurality of soft tissue mimicking thin layers with respect to each of a plurality of first distances obtained at step S400 is obtained. In this case, a ratio of "a ratio of an actual thickness value of each of a plurality of soft tissue mimicking thin layers with respect to an ultrasonic wavelength" with respect to each of a plurality of "first distances" may be obtained.

Figure 8:
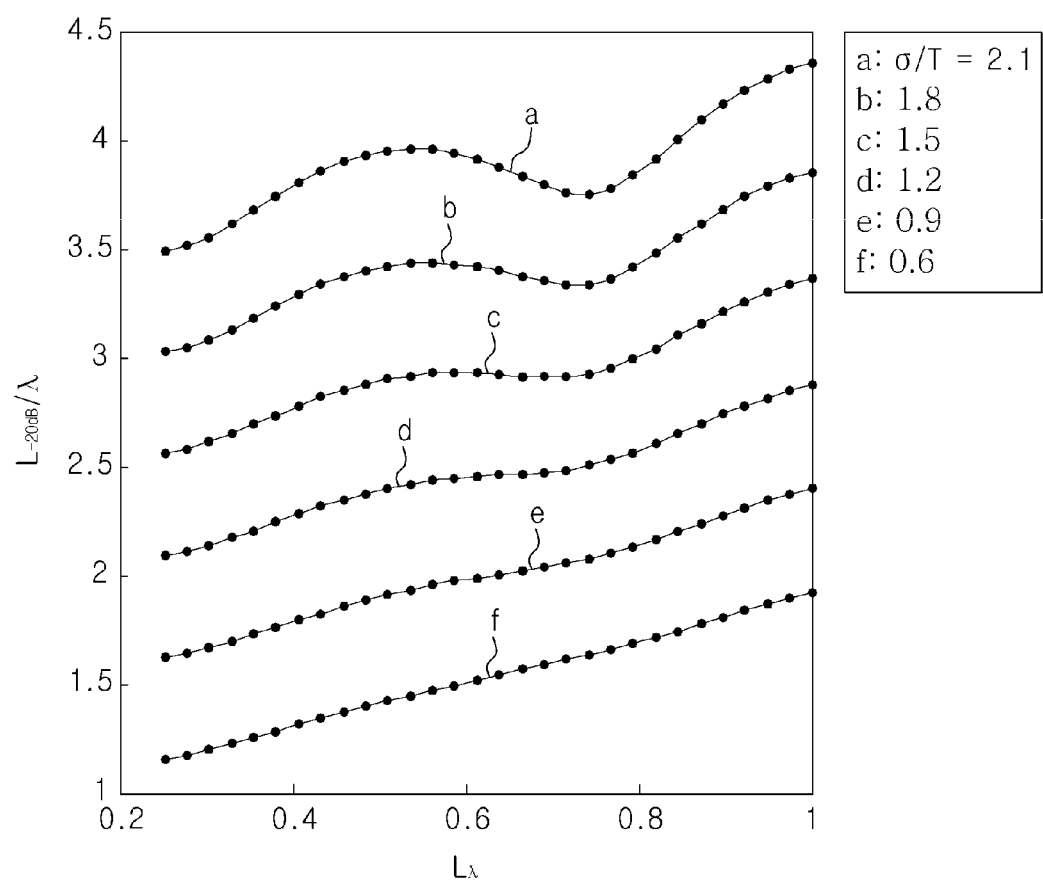
FIG. 8 is a view showing curves of "a first distance" with respect to "a ratio of an actual thickness value of each of a plurality of soft tissue mimicking thin layers with respect to an ultrasonic wavelength" depending on a width of an ultrasonic pulse according to an embodiment of the present invention.

FIG. 8 is a view showing curves expressing "a first distance" with respect to "a ratio of an actual thickness value of each of a plurality of soft tissue mimicking thin layers with respect to an ultrasonic wavelength" depending on a width of an ultrasonic pulse according to an embodiment of the present invention.

Since width of an ultrasonic pulse output from a probe of an ultrasonic imaging device may vary as described above, the curves showing "a first distance" with respect to "a ratio of an actual thickness value of each of a plurality of soft tissue mimicking thin layers with respect to an ultrasonic wavelength" may vary depending on the width of the ultrasonic pulse.

However, step S900 may be performed between steps S400 and S500.

Next, a thickness value of the measurement target object is obtained from the second distance using the acquired ratio S1000.

An actual thickness value of the measurement target object can be obtained from the second distance obtained at step S800 using a ratio of the first distance with respect to the actual thickness value of each of the plurality of soft tissue mimicking thin layers in the phantom.

In addition, if the second distance obtained at step S800 is put into the ratio curve obtained at step S900, a ratio of a thickness value of the target object with respect to an ultrasonic wavelength can be obtained, and if the ratio of the thickness value of the target object with respect to the ultrasonic wavelength is multiplied by the ultrasonic wavelength, the thickness value of the target object can be obtained.

In the phantom and a method of measuring thickness using thereof as described above, it is not that the configuration and method of the embodiment described above can be applied in a limited way, but it may be configured by selectively combining all or part of the embodiment so that various modifications can be made in the embodiment.

Meanwhile, the present invention may be implemented as a computer-readable code in a computer-readable recording medium. The computer-readable recording medium includes all kinds of recording devices in which data that can be read by a computer system is stored. Examples of the computer-readable medium include ROM, RAM, CD-ROM, a magnetic tape, a floppy disk, an optical data storage device and the like, and, in addition, it also includes a medium implemented in the form of a carrier wave (e.g., transmission through the Internet). In addition, the computer-readable recording medium may be distributed in computer systems connected through a network, and the computer-readable code can be stored and executed in a distributed manner. In addition, functional programs, codes and code segments for implementing the present invention may be easily inferred by the programmers in the art.

The present invention applying the configuration described above may provide a user with a phantom and a method of measuring thickness, which can measure thickness of a very thin target object.

Specifically, the present invention may provide a user with a phantom and a method of measuring thickness, which can measure a thickness 0.5 to 3 times as thick as an ultrasonic wavelength using an ultrasonic imaging device.

In addition, the present invention may provide a user with a method of obtaining a leading edge and a trailing edge by using Hilbert transform.

In addition, the present invention may provide a user with a phantom and a method of measuring thickness, which can measure thickness of a target object even when width of an ultrasonic wave pulse varies depending on ultrasonic imaging devices.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A phantom used for calibrating an ultrasonic image of an ultrasonic imaging device, the phantom comprising:
   a non-scattering muscle mimicking material having a flat top surface;
   a plurality of soft tissue mimicking thin layers placed in a first area, which is at least a part of a top surface of the non-scattering muscle mimicking material, and having thicknesses different from each other; and
   an anechoic blood mimicking liquid material placed in an area other than the first area among an entire area of the top surface of the non-scattering muscle mimicking material and on a top surface of the plurality of soft tissue mimicking thin layers, wherein
   gray level profiles of ultrasonic images of the top surface and a bottom surface of the plurality of soft tissue mimicking thin layers are used to calibrate the ultrasonic images.

2. The phantom according to claim 1, wherein there are four soft tissue mimicking thin layers, and thickness of each of the soft tissue mimicking thin layers is ¼, ½, ¾ or 1 time as thick as an ultrasonic wavelength generated by the ultrasonic imaging device.

3. A method of measuring thickness using an ultrasonic imaging device, the method comprising:
   a first step of obtaining a first ultrasonic image of the phantom according to claim 1;
   a second step of obtaining a first gray level profile of an elevation direction for each of a plurality of soft tissue mimicking thin layers in the first ultrasonic image;
   a third step of determining a 1-1 gray level profile for a top surface of each of the plurality of soft tissue mimicking thin layers and a 1-2 gray level profile for a bottom surface of each of the plurality of soft tissue mimicking thin layers among the plurality of first gray level profiles, and determining a leading edge which is one point of each of the plurality of 1-1 gray level profiles and a trailing edge which is one point of each of the plurality of 1-2 gray level profiles;
   a fourth step of measuring a first distance which is a distance between the leading edge and the trailing edge of each of the plurality of first gray level profiles;
   a fifth step of obtaining a second ultrasonic image of a measurement target object using the ultrasonic imaging device;
   a sixth step of obtaining a second gray level profile of an elevation direction for the second ultrasonic image;
   a seventh step of determining a 2-1 gray level profile for a top surface of the measurement target object and a 2-2 gray level profile for a bottom surface of the measurement target object among the second gray level profile, and determining a leading edge which is one point of the 2-1 gray level profile and a trailing edge which is one point of the 2-2 gray level profile;
   an eighth step of measuring a second distance which is a distance between the leading edge and the trailing edge of the determined second gray level profile;
   a ninth step of acquiring a ratio of an actual thickness value of each of the plurality of soft tissue mimicking thin layers in the phantom for the ultrasonic imaging device with respect to each of the plurality of first distances; and
   a tenth step of obtaining an actual thickness value of the measurement target object from the second distance using the acquired ratio.

4. The method according to claim 3, wherein the third step includes performing Hilbert transform on the plurality of first gray level profiles and determining the leading edge and the trailing edge of each of the plurality of first gray level profiles from a Hilbert transform value of each of the plurality of first gray level profiles, and the seventh step includes performing Hilbert transform on the second gray level profile and determining the leading edge and the trailing edge of the second gray level profile from a Hilbert transform value of the second gray level profile.

5. The method according to claim 4, wherein the third step includes determining two points corresponding to −20 dB of a maximum value among the Hilbert transform values of each of the plurality of first gray level profiles as the leading edge and the trailing edge of each of the plurality of first gray level profiles, and the seventh step includes determining two points corresponding to −20 dB of a maximum value of the Hilbert transform of the second gray level profile as the leading edge and the trailing edge of the second gray level profile.

6. The method according to claim 5, wherein the ninth step further includes a step of obtaining a curve showing actual thickness values of the plurality of soft tissue mimicking thin layers in the phantom for the ultrasonic imagimg device with respect to the plurality of first distances, and the tenth step includes obtaining a thickness value of the measurement target object from the second distance using the curve.

7. A non-transitory computer readable medium which can be read by a digital processing device, in which a program of instructions that can be executed by the digital processing device is typically implemented to perform a method of measuring thickness using an ultrasonic imaging device, the method comprising:
- a first step of obtaining a first ultrasonic image of the phantom according to claim 1;
- a second step of obtaining a first gray level profile of an elevation direction for each of a plurality of soft tissue mimicking thin layers in the first ultrasonic image;
- a third step of determining a 1-1 gray level profile for a top surface of each of the plurality of soft tissue mimicking thin layers and a 1-2 gray level profile for a bottom surface of each of the plurality of soft tissue mimicking thin layers among the plurality of first gray level profiles, and determining a leading edge which is one point of each of the plurality of 1-1 gray level profiles and a trailing edge which is one point of each of the plurality of 1-2 gray level profiles;
- a fourth step of measuring a first distance which is a distance between the leading edge and the trailing edge of each of the plurality of first gray level profiles;
- a fifth step of obtaining a second ultrasonic image of a measurement target object using the ultrasonic imaging device;
- a sixth step of obtaining a second gray level profile of an elevation direction for the second ultrasonic image;
- a seventh step of determining a 2-1 gray level profile for a top surface of the measurement target object and a 2-2 gray level profile for a bottom surface of the measurement target object among the second gray level profile, and determining a leading edge which is one point of the 2-1 gray level profile and a trailing edge which is one point of the 2-2 gray level profile;
- an eighth step of measuring a second distance which is a distance between the leading edge and the trailing edge of the determined second gray level profile;
- a ninth step of acquiring a ratio of an actual thickness value of each of the plurality of soft tissue mimicking thin layers in the phantom for the ultrasonic imaging device with respect to each of the plurality of first distances; and
- a tenth step of obtaining an actual thickness value of the measurement target object from the second distance using the acquired ratio.

* * * * *